(12) United States Patent
Barclay et al.

(10) Patent No.: US 6,568,351 B1
(45) Date of Patent: May 27, 2003

(54) METHODS FOR RAISING RABBITS

(75) Inventors: William R. Barclay, Boulder, CO (US); Archimede Mordenti, Bologna (IT); Marco Tassinari, Bologna (IT); Alessandro Zotti, Lazzanochi Saurna (IT)

(73) Assignee: Martek Biosciences Boulder Corporation, Boulder, CO (US)

( * ) Notice: Subject to any disclaimer, the term of this patent is extended or adjusted under 35 U.S.C. 154(b) by 0 days.

(21) Appl. No.: 10/181,756

(22) PCT Filed: Jan. 19, 2001

(86) PCT No.: PCT/US01/01720

§ 371 (c)(1), (2), (4) Date: Jul. 19, 2002

(87) PCT Pub. No.: WO01/53508

PCT Pub. Date: Jul. 26, 2001

Related U.S. Application Data

(60) Provisional application No. 60/177,249, filed on Jan. 20, 2000, and provisional application No. 60/177,314, filed on Jan. 21, 2000.

(51) Int. Cl.⁷ .......................... A01K 1/02; A01N 63/00
(52) U.S. Cl. ..................................... 119/483; 424/93.3
(58) Field of Search ........................ 119/483; 424/93.3

(56) References Cited

U.S. PATENT DOCUMENTS

| | | | | |
|---|---|---|---|---|
| 5,133,963 A | * | 7/1992 | Ise ........................... | 424/94.61 |
| 5,985,854 A | * | 11/1999 | Kozak ......................... | 514/75 |
| 6,103,276 A | * | 8/2000 | Pilgrim et al. ................ | 426/2 |
| 6,231,871 B1 | * | 5/2001 | Coloe ....................... | 424/258.1 |
| 2001/0046484 A1 | * | 11/2001 | Maruta et al. ............. | 424/93.3 |

* cited by examiner

Primary Examiner—Charles T. Jordan
Assistant Examiner—Elizabeth Shaw
(74) Attorney, Agent, or Firm—Sheridan Ross P.C.

(57) ABSTRACT

The present invention provides a method for raising rabbits, in particular by feeding the rabbit with a feed containing a source of long-chain fatty acid. In this manner, mortality and the feed conversion rates are decreased while average daily weight gain and long-chain fatty acid content of rabbit meat are increased compared to a rabbit raised in the absence of the long-chain fatty acid source.

44 Claims, No Drawings

METHODS FOR RAISING RABBITS

This application claims the benefit of provisional application Ser. Nos. 60/177,314 filed Jan. 21, 2000 and 60/177,249 filed Jan. 20, 2000.

The present invention is related to a method for raising rabbits, in particular by feeding the rabbit with a feed containing a source of long-chain fatty acid.

BACKGROUND OF THE INVENTION

Rabbits are grown commercially as a source of meat in many areas of the world including Italy, Spain, France, and China. Typically, the total production period is about 80–85 days divided into 3 phases: (1) weaning period—day 1 to day 30; (2) adaptation period—day 31 to day 50; and (3) grower/finishing period—day 51 to day 85. During the adaptation period the rabbits may be fed antibiotics in the feed to help maintain their health and improve weight gain and in some regions growth promoters are also used. The use of antibiotics in animal production is falling out of favor due to the development of antibiotic-resistant bacteria, as well as the movement to more natural production techniques. These compounds are generally not used in the grower/finishing period and there is a continuing need to find ways to help improve both the health and nutritional content of the rabbits especially during the grower/finisher period of production.

There is a need for a method for raising rabbits that decreases the mortality rate of the rabbits. There is also a need for a method for decreasing the feed conversion rate of rabbits. There is also a need for a method for increasing the average daily weight gain of rabbits. And there is a need for a method for increasing long-chain fatty acid (e.g., omega-3 fatty acid such as docosahexaenoic acid or DHA) content of rabbit meat.

SUMMARY OF THE INVENTION

In accordance with the present invention, a method is provided for raising a rabbit comprising feeding the rabbit a feed comprising a source of long-chain fatty acid, wherein the mortality rate of the rabbit is reduced compared to a rabbit raised in the absence of the long-chain fatty acid source.

Preferably, the long-chain fatty acid source comprises a marine source, more preferably, the long-chain fatty acid source comprises a marine source selected from the group consisting of fish oil, fish meal and microorganisms, and more preferably, the long-chain fatty acid source comprises microorganisms.

Preferably, the microorganisms are in a dry form, more preferably the microorganisms are of the order Thraustochytriales, and more preferably the microorganisms are selected from the group consisting of Thraustochytrium, Schizochytrium, and mixtures thereof.

Preferably, the long-chain fatty acid source comprises a long-chain fatty acid selected from the group consisting of linolenic acid, gammalinolenic acid, dihomogammalinolenic acid, stearidonic acid, eicosapentaenoic acid, docosapentaenoic acid (both omega-3 and omega-6 forms), docosahexaenoic acid, arachidonic acid, and mixtures thereof, more preferably, the long-chain fatty acid source comprises docosahexaenoic acid.

Preferably, the mortality rate is decreased by at least about 50% and more preferably the mortality rate is decreased by at least about 65%.

Preferably, the feed comprises at least about 0.1% by weight long-chain fatty acid source. Preferably, the feed comprises at least about 0.01% by weight long-chain omega-3 fatty acid. Preferably, the feed comprises at least about 0.003% by weight long-chain omega-6 fatty acid. Preferably, the feed is fed to the rabbit for at least about 5 days.

In accordance with the present invention, a method is provided for increasing an average daily weight gain of a rabbit comprising feeding the rabbit a feed comprising a long-chain fatty acid source, wherein the average daily weight gain of the rabbit is higher than a rabbit raised in the absence of the long-chain fatty acid source.

Preferably, the long-chain fatty acid source comprises a marine source, more preferably, the long-chain fatty acid source comprises a marine source selected from the group consisting of fish oil, fish meal and microorganisms, and more preferably, the long-chain fatty acid source comprises microorganisms.

Preferably, the microorganisms are in a dry form, more preferably the microorganisms are of the order Thraustochytriales, and more preferably the microorganisms are selected from the group consisting of Thraustochytrium, Schizochytrium, and mixtures thereof Preferably, the long-chain fatty acid source comprises a long-chain fatty acid selected from the group consisting of linolenic acid, gammalinolenic acid, dihomogammalinolenic acid, stearidonic acid, eicosapentaenoic acid, docosapentaenoic acid (both omega-3 and omega-6 forms), docosahexaenoic acid, arachidonic acid, and mixtures thereof, more preferably, the long-chain fatty acid source comprises docosahexaenoic acid.

Preferably, the average daily weight gain of the rabbit is increased by at least about 2%.

Preferably, the feed comprises at least about 0.01% by weight long-chain fatty acid source. Preferably, the feed comprises at least about 0.003% by weight long-chain omega-3 fatty acid. Preferably, the feed comprises at least about 0.003% by weight long-chain omega-6 fatty acid. Preferably, the feed is fed to the rabbit for at least about 5 days.

In accordance with the present invention, a method is provided for reducing a feed conversion rate in a rabbit comprising feeding the rabbit a feed comprising a long-chain fatty acid source, wherein the feed conversion rate of the rabbit is lower than a rabbit raised in the absence of the long-chain fatty acid source.

Preferably, the long-chain fatty acid source comprises a marine source, more preferably, the long-chain fatty acid source comprises a marine source selected from the group consisting of fish oil, fish meal and microorganisms, and more preferably, the long-chain fatty acid source comprises microorganisms.

Preferably, the microorganisms are in a dry form, more preferably the microorganisms are of the order Thraustochytriales, and more preferably the microorganisms are selected from the group consisting of Thraustochytrium, Schizochytrium, and mixtures thereof.

Preferably, the long-chain fatty acid source comprises a long-chain fatty acid selected from the group consisting of linolenic acid, gammalinolenic acid, dihomogammalinolenic acid, stearidonic acid, eicosapentaenoic acid, docosapentaenoic acid (both omega-3 and omega-6 forms), docosahexaenoic acid, arachidonic acid, and mixtures thereof, more preferably, the long-chain fatty acid source comprises docosahexaenoic acid.

Preferably, the feed conversion rate of the rabbit is decreased by at least about 0.03 g/day. Preferably, the feed conversion rate of the rabbit is decreased by at least about 1%.

Preferably, the feed comprises at least about 0.1% by weight long-chain fatty acid source. Preferably, the feed comprises at least about 0.01% by weight long-chain omega-3 fatty acid. Preferably, the feed comprises at least about 0.003% by weight long-chain omega-6 fatty acid. Preferably, the feed is fed to the rabbit for at least about 5 days.

In accordance with the present invention, a method is provided for increasing a docosahexaenoic acid content of a rabbit comprising feeding the rabbit a feed comprising a docosahexaenoic acid source. Preferably, the docosahexaenoic acid source comprises microorganisms.

Preferably, the docosahexaenoic acid source comprises a marine source. The docosahexaenoic acid source can comprise a precursor to docosahexaenoic acid such as linolenic acid, stearidonic acid, eicosapentaenoic acid, docosapentaenoic acid (n-3), or mixtures thereof. The precursors can be elongated to docosahexaenoic acid, and the precursors and the subsequent elongation products can accumulate in the rabbit meat. Preferably, the docosahexaenoic acid source comprises at least 10% (as % by weight total fatty acids) DHA.

Preferably, the microorganisms are in a dry form, more preferably the microorganisms are of the order Thraustochytriales, and more preferably the microorganisms are selected from the group consisting of Thraustochytrium, Schizochytrium, and mixtures thereof.

Preferably, the docosahexaenoic acid source comprises a long-chain fatty acid selected from the group consisting of linolenic acid, gammalinolenic acid, dihomogammalinolenic acid, stearidonic acid, eicosapentaenoic acid, docosapentaenoic acid (n-3), docosahexaenoic acid, and mixtures thereof, more preferably, the docosahexaenoic acid source comprises docosahexaenoic acid.

Preferably, the feed comprises at least about 0.1% by weight long-chain fatty acid source. Preferably, the feed comprises at least about 0.01% by weight long-chain omega-3 fatty acid. Preferably, the feed comprises at least about 0.003% by weight long-chain omega-6 fatty acid. Preferably, the feed is fed to the rabbit for at least about 5 days.

Preferably, the docosahexaenoic acid content of a thigh or loin of the rabbit is increased by at least about 50%.

In accordance with the present invention, a method is provided for increasing productivity of a rabbit comprising feeding the rabbit a feed comprising a source of long-chain fatty acid, wherein the productivity of the rabbit is higher compared to a rabbit raised in the absence of the long-chain fatty acid source.

Preferably, the productivity is increased by decreasing the mortality rate of the rabbit. Preferably, the mortality rate is decreased by at least about 40% and more preferably, the mortality rate is decreased by at least about 50%. Preferably, the productivity is increased by increasing the average daily weight gain of the rabbit. Preferably, the average daily weight gain of the rabbit is increased by at least about 1%.

Preferably, the long-chain fatty acid source comprises a marine source, more preferably, the long-chain fatty acid source comprises a marine source selected from the group consisting of fish oil, fish meal and microorganisms, and more preferably, the long-chain fatty acid source comprises microorganisms.

Preferably, the microorganisms are in a dry form, more preferably the microorganisms are of the order Thraustochytriales, and more preferably the microorganisms are selected from the group consisting of Thraustochytrium, Schizochytrium, and mixtures thereof.

Preferably, the long-chain fatty acid source comprises a long-chain fatty acid selected from the group consisting of linolenic acid, gammalinolenic acid, dihomogammalinolenic acid, stearidonic acid, eicosapentaenoic acid, docosapentaenoic acid (both omega-3 and omega-6 forms), docosahexaenoic acid, arachidonic acid, and mixtures thereof, more preferably, the long-chain fatty acid source comprises docosahexaenoic acid.

Preferably, the feed comprises at least about 0.1% by weight long-chain fatty acid source. Preferably, the feed comprises at least about 0.01% by weight long-chain omega-3 fatty acid. Preferably, the feed comprises at least about 0.003% by weight long-chain omega-6 fatty acid. Preferably, the feed is fed to the rabbit for at least about 5 days.

In accordance with the present invention, a method is provided for decreasing the total amount of fat of a rabbit comprising feeding the rabbit a feed comprising a source of long-chain fatty acid, wherein the total amount of fat of the rabbit is lower compared to a rabbit raised in the absence of the long-chain fatty acid source.

Preferably, the long-chain fatty acid source comprises a marine source, more preferably, the long-chain fatty acid source comprises a marine source selected from the group consisting of fish oil, fish meal and microorganisms, and more preferably, the long-chain fatty acid source comprises microorganisms.

Preferably, the microorganisms are in a dry form, more preferably the microorganisms are of the order Thraustochytriales, and more preferably the microorganisms are selected from the group consisting of Thraustochytrium, Schizochytrium, and mixtures thereof.

Preferably, the long-chain fatty acid source comprises a long-chain fatty acid selected from the group consisting of linolenic acid, gammalinolenic acid, dihomogammalinolenic acid, stearidonic acid, eicosapentaenoic acid, docosapentaenoic acid (both omega-3 and omega-6 forms), docosahexaenoic acid, arachidonic acid, and mixtures thereof, more preferably, the long-chain fatty acid source comprises docosahexaenoic acid.

Preferably, the total amount of fat of the rabbit is decreased by at least about 5% and more preferably the total amount of fat of the rabbit is decreased by at least about 10%.

Preferably, the feed comprises at least about 0.1% by weight long-chain fatty acid source. Preferably, the feed comprises at least about 0.01% by weight long-chain omega-3 fatty acid. Preferably, the feed comprises at least about 0.003% by weight long-chain omega-6 fatty acid. Preferably, the feed is fed to the rabbit for at least about 5 days.

In accordance with the present invention, a method is provided for raising a female rabbit for breeding comprising feeding the female rabbit a feed comprising a source of long-chain fatty acid during one or more time periods selected from the group comprising the time period prior to pregnancy, the time period during pregnancy and the time period during lactation, wherein one or more of the characteristics selected from the group comprising fertility, growth, mortality and immunity of the female rabbit or the offspring of the female rabbit is improved compared to a female rabbit or offspring raised in the absence of the long-chain fatty acid source.

Preferably, the long-chain fatty acid source comprises a marine source, more preferably, the long-chain fatty acid source comprises a marine source selected from the group consisting of fish oil, fish meal and microorganisms, and more preferably, the long-chain fatty acid source comprises microorganisms.

Preferably, the microorganisms are in a dry form, more preferably the microorganisms are of the order Thraustochytriales, and more preferably the microorganisms are selected from the group consisting of Thraustochytrium, Schizochytrium, and mixtures thereof.

Preferably, the long-chain fatty acid source comprises a long-chain fatty acid selected from the group consisting of linolenic acid, gammalinolenic acid, dihomogammalinolenic acid, stearidonic acid, eicosapentaenoic acid, docosapentaenoic acid (both omega-3 and omega-6 forms), docosahexaenoic acid, arachidonic acid, and mixtures thereof, more preferably, the long-chain fatty acid source comprises docosahexaenoic acid.

Preferably, the feed comprises at least about 0.1% by weight long-chain fatty acid source. Preferably, the feed comprises at least about 0.01% by weight long-chain omega-3 fatty acid. Preferably, the feed comprises at least about 0.003% by weight long-chain omega-6 fatty acid. Preferably, the feed is fed to the rabbit for at least about 5 days.

In accordance with the present invention, a method is provided for increasing the long-chain fatty acid content of a rabbit comprising feeding the rabbit a feed comprising a long-chain fatty acid source. Preferably, the long-chain fatty acid source comprises microorganisms.

Preferably, the long-chain fatty acid source comprises a marine source. Preferably, the long-chain fatty acid source comprises at least 10% (as % by weight total fatty acids) omega-3 long-chain fatty acid and at least 5% omega-6 long-chain fatty acid. More preferably, the long-chain fatty acid source comprises at least 15% (as % by weight total fatty acids) omega-3 long-chain fatty acid and at least 10% omega-6 long-chain fatty acid.

Preferably, the microorganisms are in a dry form, more preferably the microorganisms are of the order Thraustochytriales, and more preferably the microorganisms are selected from the group consisting of Thraustochytrium, Schizochytrium, and mixtures thereof Preferably, the long-chain fatty acid source comprises a long-chain fatty acid selected from the group consisting of linolenic acid, gammalinolenic acid, dihomogammalinolenic acid, stearidonic acid, eicosapentaenoic acid, docosapentaenoic acid (both omega-3 and omega-6 forms), docosahexaenoic acid, arachidonic acid, and mixtures thereof, more preferably, the long-chain fatty acid source comprises docosahexaenoic acid.

Preferably, the feed comprises at least about 0.1% by weight long-chain fatty acid source. Preferably, the feed comprises at least about 0.01% by weight long-chain omega-3 fatty acid. Preferably, the feed comprises at least about 0.003% by weight long-chain omega-6 fatty acid. Preferably, the feed is fed to the rabbit for at least about 5 days.

Preferably, the long-chain fatty acid content of a thigh or loin of the rabbit is increased by at least about 50%.

Preferably, the feed comprises from about 0.02% by weight to about 0.12% by weight long-chain omega-3 fatty acid, more preferably, from about 0.03% by weight to about 0.08%. Preferably, the feed comprises from about 0.008% by weight to about 0.03% by weight long-chain omega-6 fatty acid, more preferably, from about 0.01% by weight to about 0.02% by weight.

In accordance with another embodiment of the present invention, rabbit meat is provided which is produced by the methods disclosed in the present application.

DETAILED DESCRIPTION OF THE INVENTION

One embodiment of the present invention provides a method for raising a rabbit comprising feeding the rabbit a feed comprising a source of long-chain fatty acid, wherein the mortality rate of the rabbit is reduced compared to a rabbit raised in the absence of the long-chain fatty acid source. Preferably, the mortality rate is decreased by at least about 30%, more preferably by at least about 50%, and most preferably at least about 65%.

Another embodiment of the present invention provides a method for increasing an average daily weight gain of a rabbit comprising feeding the rabbit a feed comprising a long-chain fatty acid source, wherein the average daily weight gain of the rabbit is higher than a rabbit raised in the absence of the long-chain fatty acid source. Preferably, the average daily weight gain of the rabbit is increased by at least about 1%, more preferably by at least about 2%, more preferably by at least about 4%, and most preferably by at least about 6%.

Still another embodiment of the present invention provides a method for reducing a feed conversion rate in a rabbit comprising feeding the rabbit a feed comprising a long-chain fatty acid source, wherein the feed conversion rate of the rabbit is lower than a rabbit raised in the absence of the long-chain fatty acid source. Preferably, the feed conversion rate of the rabbit is decreased by at least about 0.03 g/day, more preferably by at least about 0.05 g/day, still more preferably by at least about 0.1 g/day, and most preferably by at least about 0.15 g/day. Alternatively, the feed conversion rate of the rabbit is decreased by at least about 1%, preferably by at least about 2%, and more preferably by at least about 3%.

Yet still another embodiment of the present invention provides a method for increasing productivity of a rabbit comprising feeding the rabbit a feed comprising a source of long-chain fatty acid, wherein the productivity of the rabbit is higher compared to a rabbit raised in the absence of the long-chain fatty acid source. In one aspect of the present invention, the productivity is increased by decreasing the mortality rate of the rabbit. In another aspect of the present invention, the productivity is increased by increasing the average daily weight gain of the rabbit. Preferably, the productivity is increased by both decreasing the mortality rate of the rabbit and increasing the average daily weight gain of the rabbit.

Still yet another embodiment of the present invention provides a method for increasing docosahexaenoic acid content of a rabbit comprising feeding the rabbit a feed comprising a docosahexaenoic acid source. In addition to, or as an alternative to, docosahexaenoic acid, the long-chain fatty acid source can comprise a precursor to docosahexaenoic acid such as linolenic acid, stearidonic acid, eicosapentaenoic acid, docosapentaenoic acid (n-3), or mixtures thereof. The precursors can be elongated to docosahexaenoic acid, and the precursors and the subsequent elongation products can also accumulate in the rabbit meat.

Preferably, the docosahexaenoic acid content of the loin of the rabbit is increased by at least about 50%, more preferably by at least about 100%, still more preferably by at least about 200%, and most preferably by at least about 400%.

Preferably, the docosahexaenoic acid content of the thigh of the rabbit is increased by at least about 50%, more preferably by at least about 100%, still more preferably by at least about 200%, and most preferably by at least about 400%.

Another embodiment of the present invention provides a method for decreasing the total amount of fat in rabbit meat comprising feeding the rabbit a feed comprising a long-chain fatty acid source, wherein the average total amount of fat in the resulting rabbit meat is lower than for a rabbit raised in the absence of the long-chain fatty acid source. Preferably, the average total amount of fat in the rabbit meat is decreased by at least about 5%, more preferably by at least about 10%, more preferably by at least about 15%, and most preferably by at least about 20%.

Another embodiment of the present invention provides a method for raising a female rabbit for breeding comprising feeding the female rabbit a feed which includes a source of long-chain fatty acid during one or more time periods selected from the group including the time period prior to pregnancy, the time period during pregnancy and the time period during lactation, wherein one or more of the characteristics selected from the group including fertility, growth, mortality and immunity of the female rabbit or the offspring of the female rabbit is improved compared to a female rabbit or offspring raised in the absence of the long-chain fatty acid source.

Preferably, the feed comprises at least about 0.1% by weight long-chain fatty acid source, preferably at least about 0.2%, more preferably at least about 0.4%, and more preferably at least about 0.8%. Preferably, the feed comprises at least about 0.01% by weight long-chain omega-3 fatty acid, more preferably at least about 0.015%, more preferably at least about 0.03%, and more preferably at least about 0.05%. Preferably, the feed comprises at least about 0.01% by weight DHA, more preferably at least about 0.015%, more preferably at least about 0.03%, and more preferably at least about 0.05%. Preferably, the feed comprises at least about 0.003% by weight long-chain omega-6 fatty acid, preferably at least about 0.006%, more preferably at least about 0.01%, and more preferably at least about 0.02%.

Preferably, the long-chain fatty acid source comprises a long-chain fatty acid having at least 18 carbons and at least three double bonds. Preferably, the long-chain fatty acid source comprises an omega-3 fatty acid and/or an omega-6 fatty acid. While not wishing to be bound by any theory, it has been hypothesized that feeding a rabbit a combination of omega-3 and omega-6 fatty acids can provide certain advantages. For example, it is possible that the omega-6 fatty acid contributes to the increase in growth, while the meat is being enriched with omega-3 fatty acid. Preferably, the long-chain fatty acid source comprises a long-chain omega-3 fatty acid, more preferably a long-chain omega-3 fatty acid having at least 18 carbons and at least three double bonds, and more preferably DHA. Preferably, the long-chain fatty acid source comprises at least 10% (as % by weight total fatty acids) long-chain omega-3 fatty acid (preferably DHA), more preferably at least 15%, more preferably at least 20%, and more preferably at least 40%. Preferably, the long-chain fatty acid source comprises at least 5% (as % by weight total fatty acids) long-chain omega-6 fatty acid (preferably DPA (n-6) or ARA), more preferably at least 10%, more preferably at least 20%, and more preferably at least 30%. Preferably, the long-chain fatty acid source includes at least 25% total fat, more preferably at least 35%, and more preferably at least 45%. Preferably, the ratio of long-chain omega-3 fatty acid to long-chain omega-6 fatty acid is in the range from about 1:1 to about 10:1.

The long-chain fatty acid source can be any source which comprises a long-chain fatty acid, i.e., a fatty acid containing at least about 18 carbon atoms, preferably at least about 20 carbon atoms, and more preferably at least about 22 carbons. Preferably, the long-chain fatty acid is a polyunsaturated fatty acid, ie., a fatty acid containing at least 3 unsaturated carbon-carbon bonds, preferably at least 4 unsaturated carbon-carbon bonds, more preferably at least about 5 unsaturated carbon-carbon bonds, and more preferably at least about 6 unsaturated carbon-carbon bonds. The long-chain fatty acid source can also comprise precursors to long-chain fatty acids.

Preferably, the long-chain fatty acid source comprises a long-chain fatty acid selected from the group consisting of linolenic acid (LNA), gammalinolenic acid (GLA), dihomogammalinolenic acid (DGLA), stearidonic acid (STA), eicosapentaenoic acid (EPA), docosapentaenoic acid (DPA, both omega-3 and omega-6 forms), docosahexaenoic acid (DHA), arachidonic acid (ARA), and mixtures thereof More preferably, the long-chain fatty acid source comprises docosahexaenoic acid.

The long-chain fatty acid source can include lipids, such as lipids from animal, plant and/or microbial sources. As used herein, the term "lipid" includes phospholipids; free fatty acids; esters of fatty acids; triacylglycerols; diacylglycerides; phosphatides; sterols and sterol esters; carotenoids; xanthophylls (e.g., oxycarotenoids); hydrocarbons; and other lipids. Examples of animal sources include aquatic animals (e.g., fish, marine mammals, crustaceans, etc.) and lipids extracted from animal tissues (e.g., brain, liver, eyes, etc.). Examples of plant sources include macroalgae, flax seeds, rapeseeds, evening primrose, soy and borage. Examples of microorganisms include microalgae, protists and fungi (including yeast).

Preferably, the long-chain fatty acid source comprises a marine source selected from the group consisting of fish oil, fish meal and microorganisms. The use of a microorganism source, such as algae, provides organoleptic advantages, i.e., meat from rabbits consuming fatty acids from a microorganism source does not have the fishy taste and smell (organoleptic problems) that meat from rabbits consuming fatty acids from a fish source tends to have. More preferably, the long-chain fatty acid source comprises microorganisms. Preferably, the microorganisms are of the order Thraustochytriales. More preferably, the microorganisms are selected from the group consisting of Thraustochytrium, Schizochytrium, and mixtures thereof. It should be noted that many experts agree that Ulkenia is not a separate genus, but is in fact part of the genus Schizochytrium. As used herein, the genus Schizochytrium will include Ulkenia. Information regarding such microorganisms can be found in U.S. Pat. Nos. 5,130,242 and 5,340,594, which are incorporated herein by reference in their entirety. When the long-chain fatty acid source comprises microorganisms, the microorganisms are preferably in a dry form, more preferably a whole cell dry form.

The long-chain fatty acid source is preferably fed to rabbits for at least about 5 days, more preferably at least about 10 days, more preferably at least about 20 days, and more preferably at least about 35 days. Although the rabbits are typically fed during the grower/finishing period, the rabbits can also be fed during the adaptation period (e.g., to increase the immune response of the rabbit) or during the weaning period (e.g., long-chain fatty acids can be fed to the mother during weaning of the baby rabbits in order to pass on the benefits to the babies).

Alternatively, the long-chain fatty acid(s) can be extracted from a source and, preferably, microencapsulated. Lipids containing the desired long-chain fatty acid(s) can be extracted from the various sources by any suitable means, such as by supercritical fluid extraction or by extraction with solvents such as chloroform, hexane, methylene chloride, methanol and the like. Alternatively, the lipids may be extracted using solventless extraction techniques, such as are described in U.S. Provisional Patent Application Ser. No. 60/177,125 entitled "SOLVENTLESS EXTRACTION PROCESS" filed Jan. 19,2000, U.S. patent application Ser. No. 09/766,50 entitled "SOLVENTLESS EXTRACTION PROCESS" filed Jan. 19, 2001, and PCT Patent Application Ser. No. PCT/US01/01806 entitled "SOLVENTLESS EXTRACTION PROCESS" filed Jan. 19, 2001, which are incorporated herein by reference in their entirety. The extracted lipids can be evaporated under reduced pressure to produce a sample of concentrated lipid material.

A typical pelletized rabbit ration fed during the grower/finishing period is outlined as follows:

| | |
|---|---|
| Wheat middlings | 22.00% |
| Dehydrated alfalfa hay | 28.00% |
| Barley meal | 15.75% |
| Dry beet pulp | 10.00% |
| Soy-bean meal | 7.90% |
| Sunflower meal | 7.00% |
| Soy-bean hulls | 4.80% |
| Sugar cane molasses | 2.00% |
| Soy-bean oil | 0.90% |
| Dicalcium phosphate | 0.45% |
| Vitamin-mineral premix | 1.00% |

This ration is pelletized (at temperatures of 70–90° C.) into pellets of about 3mm in diameter and 1–1.5 cm long.

As can be seen, there are no sources of long-chain omega-3 fatty acids in this typical rabbit ration. While conducting research (feeding trials) investigating ways to enrich rabbit meat with long-chain omega-3 fatty acids, we have discovered that adding a source of these fatty acids to the rabbits feed ration can also increase overall productivity. We have found that providing a source of long-chain omega-3 fatty acids in the feed of production rabbits during the grower/finishing stage of production not only results in enrichment of the rabbit meat with long-chain omega-3 fatty acids, it can also decrease rabbit mortality, improve average daily weight gain and improve feed conversion efficiency.

EXAMPLES

Example 1

After the adaptation period, 300 rabbits (50 days old) were randomly divided into three groups, homogenous for age, sex and weight. The animals were placed in cages (2 animals per cage). Feed and water were provided ad libitum. Each rabbit was weighed at the beginning of the feeding period (age=50 days old) and at the end of the feeding period (age=82 days old). At the end of the feeding period 24 animals (4 males and 4 females of similar weight from each group) were sacrificed and the left thigh and loin were collected for further analyses. Mortality and feed consumption were recorded throughout the trial. One group (labeled control—consisting of 100 rabbits) was fed the typical pelletized diet outlined above except with an additional 0.2% of a vitamin E premix added. A second group was fed the same diet as in the control treatment except with 0.4% of a dried whole-cell microalgal source of the long-chain omega-3 fatty acid (DHA—docosahexaenoic acid; C22:6n-3) added to the pelletized ration. The third group of 100 rabbits was fed the same diet as in the control treatment except with 0.8% of the dried whole-cell microalgal source added to the pelletized ration. The DHA content of the dried microalgae was about 17% of cellular dry weight. The microalgae also contained about 5% (as % cellular dry weight) of the long-chain omega-6 fatty acid (DPA—docosapentaenoic acid; C22:5n-6).

The final composition of each of the three rations is summarized in Table 1.

TABLE 1

Composition of the experimental rations (% weight)

| | Control (%) | Low DHA (%) | Higher DHA (%) |
|---|---|---|---|
| Wheat middlings | 22.00 | 22.00 | 22.00 |
| Dehydrated alfalfa hay | 28.00 | 28.00 | 28.00 |
| Barley meal | 15.75 | 15.75 | 15.75 |
| Dry beet pulp | 10.00 | 10.00 | 10.00 |
| Soy-bean meal | 7.90 | 7.90 | 7.90 |
| Sunflower meal | 7.00 | 7.00 | 7.00 |
| Soy-bean hulls | 4.80 | 4.65 | 4.50 |
| Sugar cane molasses | 2.00 | 2.00 | 2.00 |
| Soy-bean oil | 0.90 | 0.45 | 0.00 |
| Dicalcium phosphate | 0.45 | 0.45 | 0.45 |
| Vitamin E premix | 0.20 | 0.20 | 0.20 |
| Vitamin-mineral premix | 1.00 | 1.00 | 1.00 |

The results of feeding these rations to the rabbits are summarized below in Tables 2–4.

TABLE 2

Live weight at beginning and end of trial, average daily weight gain (ADG), and feed conversion rate (FCR = weight feed consumed/weight gained).

| | Control diet | Low-level DHA | Higher-level DHA |
|---|---|---|---|
| Live weight | | | |
| beginning (g ± SD) | 1796.6 ± 132.8 | 1754.5 ± 138.1 | 1769.7 ± 12.3 |
| end (g ± SD) | 2792.9 ± 164.3 | 2840.3 ± 184.9 | 2817.5 ± 150.2 |
| ADG (g/day ± SD) | 31.1 ± 3.4[a] | 33.9 ± 3.4[b] | 32.7 ± 2.8[ab] |
| FCR (g/g) | 3.95 | 3.80 | 3.82 |
| Dressing Percentages (% ± SD) | 58.96 ± 1.49 | 58.49 ± 1.53 | 58.41 ± 2.01 |
| Mortality (%) | 3.0 | 1.0 | 1.0 |

[ab]different letters in the same row indicate significant difference at $P < 0.01$ level.

TABLE 3

Example DHA content (% fat and mg DHA/100 mg meat) of the resulting rabbit meat.

| | Control diet | Low-level DHA | Higher-level DHA |
|---|---|---|---|
| Rabbit Loin | | | |
| DHA % fat | 0.64 ± 0.14[a] | 1.94 ± 0.32[b] | 3.32 ± 0.92[c] |
| mg DHA/100 g meat | 12 | 34 | 53 |
| Rabbit thigh | | | |
| DHA % fat | 0.52 ± 0.21[a] | 1.56 ± 0.39[b] | 2.62 ± 0.78[c] |
| mg DHA/100 g meat | 20 | 59 | 93 |

[abc]different letters in the same row indicate significant difference at $P < 0.01$ level.

TABLE 4

Long-chain omega-3 and omega-6 fatty acid content (as % total fatty acids) of the rabbit meat from the feeding trial.
The data are mean contents from 8 rabbits.

|  | Control | low-level DHA | higher-level DHA |
|---|---|---|---|
| Rabbit loin |  |  |  |
| DHA (n-3) | 0.66 | 1.93 | 3.32 |
| EPA (n-3) | 0.16 | 0.23 | 0.28 |
| DPA (n-3) | 0.75 | 1.17 | 0.83 |
| DPA (n-6) | 0.56 | 0.75 | 1.00 |
| Rabbit thigh |  |  |  |
| DHA (n-3) | 0.52 | 1.58 | 2.65 |
| EPA (n-3) | 0.16 | 0.23 | 0.28 |
| DPA (n-3) | 0.67 | 0.64 | 0.79 |
| DPA (n-6) | 0.26 | 0.68 | 0.77 |

In addition to the DHA enrichment, the DHA fed rabbits thighs and loins were enriched in EPA and in DPA(n-3) and DPA(n-6) long-chain fatty acids as compared to the control meat samples. The low-level DHA feed rabbit thighs were not enriched in the DPA(n-3) long-chain fatty acid, but the higher-level DHA feed thighs were enriched in this fatty acid.

As an example of the improved productivity of the rabbits fed a source of long-chain omega-3 fatty acid, one can readily calculate from the above data that the combination of lower mortality and increased weight gain (about 2 g/rabbit/day) in the low DHA treatment resulted in about a 4% increase in overall rabbit production. Surprisingly, the low-level DHA feed provides as good results as the higher-level DHA feed in many cases, and in some cases provides even better results than the higher-level DHA feed. At the same time there were significant increases in the DHA content of the rabbit meat, increasing its overall nutritional value for humans.

Table 5 sets forth the experimental protocol that was used to generate subsequent data in Tables 6–12.

TABLE 5

Rabbit Trial: experimental plan

| Animals | n° | 300 (150 m + 150 f) |
|---|---|---|
| Animals x cage | n° | 2 |
| Experimental groups | n° | 3 |
| Trial duration | d | 32 |
| Initial age | d | 50 |
| Initial average body weight | g | 1765 |
| Slaughtering trials | n° rabbits | 24 (12 m + 12 f) |
| Control feed consumption | n° rabbits | 300 |
| Control average daily gain | n° rabbits | 300 |
| Mortality (32 d exp. per.) | n° rabbits | 300 |

Table 6 sets forth the total DHA content as % of fat in experimental diets.

TABLE 6

Rabbit Trial: experimental diets

| Experimental groups | Total DHA content (% Fat) |
|---|---|
| Control | 0.18 |
| Low Level (Marine Algae* 0.4%) | 2.15 |
| High Level (Marine Algae* 0.8%) | 3.11 |

*Marine algae - Schizochytrium sp.: DHA-Gold ™ OmegaTech Inc.

Table 7 sets forth the fatty acid composition of the experimental diets and of algae, where D.M. is dry matter and C22:6n3 is docosahexaenoic acid (DHA).

TABLE 7

Rabbit Trial: Fatty Acid composition of the experimental diets and of algae

|  |  | Control | Low Level | High Level | Algae(*) |
|---|---|---|---|---|---|
| D.M. | % | 90.28 | 90.56 | 90.29 | 96.90 |
| Fat | % DM | 3.14 | 3.35 | 3.21 | 54.22 |
| C22:6n3 | % Fat | 0.18 | 2.15 | 3.11 | 35.06 |

(*)Marine algae - Schizochytrium sp.: DHA-Gold ™ OmegaTech Inc.

Table 8 sets forth the chemical composition of the experimental diets as a percent of dry matter, where ether extract is approximately equal to the amount of lipids in the diets.

TABLE 8

Rabbit Trial: Chemical composition of the experimental diets

|  |  | Control | Low Level | High Level |
|---|---|---|---|---|
| Dry matter | % | 90.28 | 90.56 | 90.29 |
| Crude protein | % DM | 17.47 | 17.44 | 17.85 |
| Ether extract | % DM | 3.14 | 3.35 | 3.21 |
| Crude fiber | % DM | 16.06 | 16.86 | 16.88 |
| Ashes | % DM | 8.30 | 7.89 | 8.03 |
| NDF | % DM | 37.38 | 36.65 | 36.18 |
| ADF | % DM | 21.73 | 22.77 | 21.38 |
| Starch | % DM | 17.41 | 17.19 | 18.00 |
| Calcium | % DM | 1.06 | 1.05 | 1.06 |
| Phosphorus | % DM | 0.59 | 0.54 | 0.55 |

Table 9 sets forth the chemical analysis and fat composition of the rabbit loin samples of Table 3 for rabbits fed control feed, and feed containing a low level of long-chain fatty acid and a higher level of long-chain fatty acid.

TABLE 9

Rabbit Trial: Chemical analysis and fatty acids composition of rabbit loin samples (means ± S.D.)

|  |  | Control | Low Level | High Level |
|---|---|---|---|---|
| D.M. | % | 26.56 ± 0.41 | 26.52 ± 0.64 | 26.17 ± 0.92 |
| Fat | % DM | 6.83 ± 2.11 | 6.69 ± 1.28 | 6.08 ± 2.32 |

Table 10 shows chemical analysis of fatty acids composition of the rabbit thigh samples of Table 3 for rabbits fed control feed, and feed containing a low level of long-chain fatty acids and a higher level of long-chain fatty acids.

TABLE 10

Rabbit Trial: chemical analysis and fatty acids composition of Rabbit Thigh samples (means ± S.D.)

|  |  | Control | Low Level | High Level |
|---|---|---|---|---|
| D.M. | % | 27.89 ± 1.40 | 27.84 ± 1.19 | 27.23 ± 1.50 |
| Fat | % DM | 13.96 ± 4.51 | 13.68 ± 3.16 | 13.04 ± 5.13 |
| C22:6n3 | % Fat | 0.52 ± 0.21$^A$ | 1.56 ± 0.39$^B$ | 2.62 ± 0.78$^C$ |
| mg DHA/100 g meat |  | 20 | 59 | 93 |

$^{ABC}$different letters in the same row are significantly different (P < 0.01)

Table 11 shows detailed chemical analysis of fatty acids composition of rabbit loin samples for rabbits fed control feed, and feed containing low-level long-chain fatty acid source and higher-level long-chain fatty acid source.

TABLE 11

Rabbit Loin

CONTROL

| Filename | L274 | L282 | L283 | L284 | L285 | L286 | L287 | L288 |
|---|---|---|---|---|---|---|---|---|
| C14:0 | 5.23 | 4.80 | 4.85 | 5.82 | 4.69 | 4.60 | 4.74 | 4.22 |
| C14:1 | 0.57 | 0.85 | 0.58 | 0.53 | 1.04 | 0.51 | 0.67 | 0.62 |
| C16:0 | 29.87 | 30.98 | 26.76 | 30.12 | 27.51 | 29.26 | 26.84 | 25.51 |
| C16:1 | 4.01 | 5.56 | 8.32 | 4.33 | 7.11 | 2.97 | 4.55 | 8.14 |
| C18:0 | 6.43 | 8.54 | 5.61 | 5.43 | 5.23 | 7.50 | 5.78 | 6.65 |
| C18:1 | 20.14 | 21.29 | 19.01 | 17.38 | 20.28 | 17.75 | 18.62 | 20.31 |
| C18:2 | 25.17 | 20.62 | 28.96 | 25.76 | 23.77 | 25.55 | 26.58 | 29.18 |
| C20:0 | 0.00 | 0.00 | 0.00 | 0.00 | 0.00 | 0.00 | 0.00 | 0.00 |
| C18:3 | 4.01 | 2.51 | 5.05 | 4.09 | 3.92 | 3.30 | 3.73 | 4.75 |
| C20:1 | 0.00 | 0.00 | 0.15 | 0.11 | 0.13 | 0.00 | 0.13 | 0.00 |
| C18:4n3 | 0.00 | 0.00 | 0.00 | 0.00 | 0.00 | 0.00 | 0.00 | 0.00 |
| C20:2 | 0.55 | 0.60 | 0.62 | 0.52 | 0.78 | 0.65 | 0.55 | 0.00 |
| C22:0 | 0.00 | 0.00 | 0.00 | 0.00 | 0.00 | 0.00 | 0.00 | 0.00 |
| C20:3 | 2.24 | 2.76 | 2.78 | 3.19 | 2.54 | 4.43 | 4.14 | 3.01 |
| C20:4 | 0.00 | 0.00 | 0.00 | 0.07 | 0.00 | 0.00 | 0.00 | 0.00 |
| C22:1 | 0.00 | 0.00 | 0.00 | 0.00 | 0.00 | 0.00 | 0.00 | 0.00 |
| C20:5 | 0.00 | 0.00 | 0.23 | 0.28 | 0.19 | 0.30 | 0.28 | 0.00 |
| C24:0 | 0.00 | 0.00 | 0.00 | 0.00 | 0.06 | 0.00 | 0.05 | 0.00 |
| C24:1 | 0.49 | 0.58 | 0.44 | 0.55 | 0.52 | 0.75 | 0.72 | 0.65 |
| C22:5n6 | 0.30 | 0.62 | 0.45 | 0.32 | 0.57 | 1.01 | 0.50 | 0.72 |
| C22:5n3 | 0.42 | 0.40 | 0.58 | 0.98 | 1.16 | 0.67 | 1.32 | 0.45 |
| C22:6n3 | 0.57 | 0.42 | 0.64 | 0.80 | 0.51 | 0.74 | 0.81 | 0.79 |
| SUM | 100 | 100 | 100 | 100 | 100 | 100 | 100 | 100 |

HIGH LEVEL

| Filename | L251 | L252 | L253 | L254 | L255 | L256 | L257 | L258 |
|---|---|---|---|---|---|---|---|---|
| C14:0 | 2.77 | 4.75 | 7.33 | 5.59 | 6.37 | 5.29 | 5.50 | 4.00 |
| C14:1 | 0.00 | 0.61 | 2.84 | 0.75 | 0.99 | 0.45 | 0.77 | 0.66 |
| C16:0 | 29.59 | 28.40 | 27.71 | 29.96 | 29.77 | 26.29 | 31.80 | 25.99 |
| C16:1 | 1.54 | 3.06 | 8.75 | 4.17 | 8.74 | 2.53 | 4.85 | 3.92 |
| C18:0 | 11.96 | 8.10 | 5.50 | 6.50 | 6.02 | 5.73 | 0.46 | 6.14 |
| C18:1 | 17.04 | 15.25 | 16.01 | 18.85 | 16.95 | 16.20 | 15.18 | 15.44 |
| C18:2 | 17.58 | 24.08 | 21.00 | 25.44 | 19.46 | 29.43 | 25.39 | 25.76 |
| C20.0 | 0.00 | 0.00 | 0.00 | 0.00 | 0.00 | 0.00 | 0.00 | 0.00 |
| C18:3n-3 | 2.18 | 3.19 | 3.52 | 4.37 | 3.06 | 5.13 | 3.56 | 3.32 |
| C20:1 | 0.00 | 0.00 | 0.00 | 0.00 | 0.00 | 0.00 | 0.00 | 0.00 |
| C18:4n3 | 0.00 | 0.00 | 0.00 | 0.00 | 0.00 | 0.00 | 0.00 | 0.00 |
| C20:2 | 0.00 | 0.00 | 0.43 | 0.47 | 0.50 | 0.39 | 0.45 | 0.45 |
| C22:0 | 0.00 | 0.00 | 0.00 | 0.00 | 0.00 | 0.00 | 0.00 | 0.00 |
| C20:3 | 5.17 | 5.49 | 2.68 | 1.80 | 3.00 | 3.00 | 4.84 | 5.39 |
| C20:4n-6 | 0.00 | 0.00 | 0.00 | 0.00 | 0.00 | 0.00 | 0.00 | 0.00 |
| C22:1 | 0.00 | 0.00 | 0.00 | 0.00 | 0.00 | 0.00 | 0.00 | 0.00 |
| C20:5n-3 | 0.83 | 0.65 | 0.35 | 0.33 | 0.38 | 0.32 | 0.40 | 0.48 |
| C:24:0 | 4.90 | 0.00 | 0.00 | 0.00 | 0.00 | 0.00 | 0.00 | 0.00 |
| C24:1 | 0.38 | 0.63 | 0.34 | 0.22 | 0.33 | 0.34 | 0.56 | 0.54 |
| C22:5n6 | 1.09 | 1.20 | 0.83 | 0.66 | 0.76 | 0.88 | 1.17 | 1.44 |
| C22:5n3 | 0.70 | 0.93 | 0.44 | 0.38 | 0.41 | 0.81 | 0.92 | 2.04 |
| C22:6n3 | 4.18 | 3.68 | 2.29 | 2.39 | 2.23 | 3.22 | 4.15 | 4.42 |
| SUM | 100 | 100 | 100 | 100 | 100 | 100 | 100 | 100 |

LOW LEVEL

| Filename | L279 | L280 | L281 | L289 | L290 | L291 | L292 | L293 |
|---|---|---|---|---|---|---|---|---|
| C14:0 | 4.52 | 5.00 | 4.31 | 3.97 | 5.03 | 5.31 | 4.10 | 4.48 |
| C14:1 | 0.40 | 0.65 | 0.92 | 0.70 | 0.61 | 0.84 | 0.82 | 0.62 |
| C16:0 | 28.36 | 26.83 | 27.47 | 27.35 | 27.18 | 25.06 | 26.88 | 29.12 |
| C16:1 | 2.96 | 3.83 | 5.33 | 2.70 | 3.50 | 3.51 | 5.22 | 4.81 |
| C18:0 | 5.78 | 5.31 | 6.07 | 5.87 | 5.47 | 5.85 | 5.42 | 6.58 |
| C18:1 | 17.58 | 17.49 | 17.52 | 15.65 | 16.48 | 16.92 | 17.76 | 18.68 |
| C18:2 | 27.38 | 26.68 | 26.01 | 28.75 | 29.23 | 23.52 | 28.50 | 23.18 |
| C20:0 | 0.00 | 0.00 | 0.00 | 0.00 | 0.00 | 0.00 | 0.00 | 0.00 |
| C18:3 | 4.09 | 4.65 | 4.09 | 4.32 | 5.01 | 5.39 | 3.91 | 3.09 |
| C20:1 | 0.12 | 0.11 | 0.11 | 0.11 | 0.00 | 0.00 | 0.12 | 0.00 |
| C18:4n3 | 0.00 | 0.00 | 0.00 | 0.00 | 0.00 | 0.00 | 0.00 | 0.00 |
| C20:2 | 0.57 | 0.40 | 0.43 | 0.00 | 0.52 | 0.48 | 0.48 | 0.59 |
| C22:0 | 0.00 | 0.00 | 0.00 | 0.00 | 0.00 | 0.00 | 0.00 | 0.00 |
| C20:3 | 3.51 | 2.73 | 3.28 | 4.64 | 2.77 | 2.47 | 3.69 | 3.81 |
| C20:4 | 0.00 | 0.00 | 0.00 | 0.00 | 0.00 | 0.00 | 0.00 | 0.00 |
| C22:1 | 0.00 | 0.00 | 0.00 | 0.00 | 0.00 | 0.00 | 0.00 | 0.00 |
| C20:5 | 0.33 | 0.25 | 0.30 | 0.30 | 0.32 | 0.31 | 0.32 | 0.30 |

TABLE 11-continued

Rabbit Loin

| | | | | | | | | |
|---|---|---|---|---|---|---|---|---|
| C:24:0 | 0.00 | 0.00 | 0.00 | 0.00 | 0.00 | 0.00 | 0.00 | 0.00 |
| C24:1 | 0.51 | 0.40 | 0.48 | 0.61 | 0.39 | 0.40 | 0.57 | 0.54 |
| C22:5n-6 | 0.63 | 0.54 | 0.71 | 0.67 | 1.25 | 0.57 | 0.75 | 0.71 |
| C22:5n-3 | 1.41 | 1.16 | 1.24 | 1.46 | 0.58 | 0.58 | 1.40 | 1.57 |
| C22:6n-3 | 1.87 | 1.79 | 1.71 | 2.68 | 1.70 | 1.80 | 2.06 | 1.90 |
| SUM | 100 | 100 | 100 | 100 | 100 | 100 | 100 | 100 |

Table 12 shows detailed chemical analysis of fatty acids composition of rabbit thigh samples for rabbits fed control feed, and feed containing low-level long-chain fatty acid source and higher-level long-chain fatty acid source.

TABLE 12

Rabbit Thigh

CONTROL

| Filename | T274 | T282 | T283 | T284 | T285 | T286 | T287 | T288 |
|---|---|---|---|---|---|---|---|---|
| C14:0 | 4.19 | 4.38 | 4.41 | 5.37 | 3.28 | 4.21 | 4.48 | 3.49 |
| C14:1 | 0.55 | 0.87 | 0.52 | 0.50 | 0.65 | 0.44 | 0.60 | 0.45 |
| C16:0 | 29.57 | 27.86 | 27.06 | 29.77 | 27.62 | 27.69 | 28.22 | 24.12 |
| C16:1 | 4.72 | 6.33 | 3.43 | 3.75 | 5.79 | 3.27 | 4.53 | 2.74 |
| C18:0 | 5.69 | 5.96 | 6.15 | 5.84 | 6.70 | 6.89 | 6.41 | 6.23 |
| C18:1 | 21.47 | 22.48 | 19.59 | 18.35 | 24.83 | 19.15 | 20.36 | 17.77 |
| C18:2 | 25.91 | 24.63 | 28.35 | 26.74 | 24.00 | 29.08 | 27.13 | 32.86 |
| C20.0 | 0.05 | 0.00 | 0.00 | 0.00 | 0.00 | 0.00 | 0.05 | 0.00 |
| C18:3n-3 | 4.19 | 4.17 | 4.60 | 4.47 | 3.72 | 4.50 | 4.41 | 4.80 |
| C20:1 | 0.24 | 0.20 | 0.22 | 0.16 | 0.24 | 0.00 | 0.00 | 0.00 |
| C18:4n-3 | 0.00 | 0.00 | 0.00 | 0.00 | 0.00 | 0.00 | 0.00 | 0.00 |
| C20:2 | 0.60 | 0.45 | 0.48 | 0.58 | 0.68 | 0.55 | 0.71 | 0.57 |
| C22:0 | 0.00 | 0.00 | 0.00 | 0.00 | 0.00 | 0.00 | 0.00 | 0.00 |
| C20:3 | 1.48 | 1.17 | 2.36 | 2.10 | 1.05 | 2.37 | 1.73 | 3.64 |
| C20:4n-6 | 0.00 | 0.00 | 0.00 | 0.00 | 0.04 | 0.04 | 0.00 | 0.00 |
| C22:1 | 0.00 | 0.00 | 0.00 | 0.00 | 0.00 | 0.00 | 0.00 | 0.00 |
| C20:5n-3 | 0.12 | 0.11 | 0.19 | 0.16 | 0.08 | 0.16 | 0.12 | 0.27 |
| C24:0 | 0.00 | 0.04 | 0.00 | 0.00 | 0.14 | 0.00 | 0.05 | 0.00 |
| C24:1 | 0.34 | 0.29 | 0.46 | 0.40 | 0.39 | 0.47 | 0.00 | 0.68 |
| C22:5n-6 | 0.19 | 0.18 | 0.31 | 0.22 | 0.17 | 0.28 | 0.28 | 0.47 |
| C22:5n-3 | 0.37 | 0.58 | 1.28 | 1.12 | 0.33 | 0.53 | 0.39 | 0.77 |
| C22:6n-3 | 0.39 | 0.31 | 0.58 | 0.47 | 0.31 | 0.59 | 0.52 | 0.96 |
| SUM | 100 | 100 | 100 | 100 | 100 | 100 | 100 | |

HIGH LEVEL

| Filename | T251 | T252 | T253 | T254 | T255 | T256 | T257 | T258 |
|---|---|---|---|---|---|---|---|---|
| C14:0 | 3.68 | 4.75 | 5.18 | 4.63 | 5.06 | 5.18 | 5.06 | 6.13 |
| C14:1 | 0.39 | 0.72 | 1.75 | 0.66 | 0.91 | 0.56 | 0.65 | 0.85 |
| C16:0 | 26.85 | 26.91 | 26.46 | 28.92 | 31.39 | 26.21 | 29.15 | 27.04 |
| C16:1 | 2.39 | 3.47 | 7.77 | 4.55 | 6.50 | 2.93 | 4.05 | 3.58 |
| C18:0 | 6.72 | 6.59 | 5.06 | 6.14 | 6.61 | 6.25 | 5.94 | 6.16 |
| C18:1 | 15.29 | 16.50 | 18.26 | 18.35 | 18.32 | 15.88 | 16.72 | 15.80 |
| C18:2 | 28.07 | 27.94 | 25.22 | 25.80 | 21.95 | 28.91 | 26.93 | 28.11 |
| C20.0 | 0.00 | 0.00 | 0.00 | 0.00 | 0.00 | 0.00 | 0.00 | 0.00 |
| C18:3 | 3.72 | 4.67 | 4.43 | 4.29 | 3.77 | 4.76 | 4.40 | 4.81 |
| C20:1 | 0.11 | 0.00 | 0.15 | 0.13 | 0.16 | 0.12 | 0.16 | 0.00 |
| C18:4n3 | 0.00 | 0.00 | 0.00 | 0.00 | 0.00 | 0.00 | 0.00 | 0.00 |
| C20:2 | 0.42 | 0.60 | 0.00 | 0.48 | 0.46 | 0.38 | 0.57 | 0.33 |
| C22:0 | 0.00 | 0.00 | 0.00 | 0.00 | 0.00 | 0.00 | 0.00 | 0.00 |
| C20:3 | 4.85 | 2.61 | 1.70 | 1.93 | 1.35 | 3.31 | 2.09 | 2.68 |
| C20:4 | 0.00 | 0.00 | 0.00 | 0.00 | 0.00 | 0.00 | 0.00 | 0.00 |
| C22:1 | 0.00 | 0.00 | 0.00 | 0.00 | 0.03 | 0.00 | 0.00 | 0.00 |
| C20:5 | 0.40 | 0.32 | 0.22 | 0.24 | 0.18 | 0.33 | 0.20 | 0.31 |
| C24:0 | 0.00 | 0.00 | 0.00 | 0.05 | 0.03 | 0.00 | 0.00 | 0.00 |
| C24:1 | 0.50 | 0.36 | 0.32 | 0.34 | 0.26 | 0.41 | 0.38 | 0.32 |
| C22:5n6 | 1.06 | 0.78 | 0.68 | 0.70 | 0.58 | 0.91 | 0.78 | 0.75 |
| C22:5n3 | 1.31 | 1.22 | 0.83 | 0.45 | 0.75 | 0.76 | 0.47 | 0.52 |
| C22:6n3 | 4.25 | 2.54 | 2.01 | 2.34 | 1.68 | 3.1 | 2.43 | 2.81 |
| SUM | 100 | 100 | 100 | 100 | 100 | 100 | 100 | 100 |

TABLE 12-continued

Rabbit Thigh

| | LOW LEVEL | | | | | | | |
|---|---|---|---|---|---|---|---|---|
| Filename | T279 | T280 | T281 | T289 | T290 | T291 | T292 | T293 |
| C14:0 | 5.20 | 4.96 | 4.50 | 7.03 | 5.44 | 4.15 | 5.04 | 4.13 |
| C14:1 | 0.54 | 0.70 | 0.84 | 1.34 | 0.71 | 0.67 | 0.92 | 0.46 |
| C16:0 | 29.20 | 28.20 | 27.81 | 29.65 | 31.09 | 24.91 | 33.78 | 28.61 |
| C16:1 | 3.32 | 3.63 | 4.75 | 4.57 | 4.60 | 3.51 | 6.09 | 4.23 |
| C18:0 | 6.68 | 5.75 | 6.77 | 5.23 | 6.61 | 6.09 | 7.69 | 6.39 |
| C18:1 | 16.20 | 17.63 | 19.60 | 1.20 | 1.18 | 18.54 | 1.78 | 21.21 |
| C18:2 | 26.68 | 26.82 | 26.92 | 35.61 | 36.52 | 30.77 | 33.04 | 25.71 |
| C20:0 | 0.00 | 0.00 | 0.08 | 0.00 | 0.00 | 0.00 | 0.00 | 0.00 |
| C18:3 | 4.33 | 4.57 | 4.63 | 6.53 | 6.65 | 5.38 | 5.16 | 4.10 |
| C20:1 | 0.16 | 0.00 | 0.19 | 0.00 | 0.00 | 0.00 | 0.00 | 0.00 |
| C18:4n3 | 0.00 | 0.00 | 0.00 | 0.00 | 0.00 | 0.00 | 0.00 | 0.00 |
| C20:2 | 0.58 | 0.89 | 0.56 | 0.73 | 0.60 | 0.47 | 0.72 | 0.58 |
| C22:0 | 0.00 | 0.00 | 0.00 | 0.00 | 0.00 | 0.00 | 0.00 | 0.00 |
| C20:3 | 2.18 | 2.95 | 1.01 | 8.69 | 2.14 | 2.22 | 2.77 | 2.06 |
| C20:4 | 0.00 | 0.00 | 0.00 | 0.00 | 0.00 | 0.00 | 0.00 | 0.00 |
| C22:1 | 0.00 | 0.00 | 0.00 | 0.00 | 0.00 | 0.00 | 0.00 | 0.00 |
| C20:5 | 0.23 | 0.28 | 0.18 | 0.32 | 0.23 | 0.22 | 0.25 | 0.17 |
| C24:0 | 0.11 | 0.00 | 0.00 | 0.00 | 0.15 | 0.00 | 0.00 | 0.00 |
| C24:1 | 0.43 | 0.48 | 0.21 | 0.48 | 0.00 | 0.39 | 0.00 | 0.00 |
| C22:5n6 | 0.46 | 0.48 | 0.36 | 0.64 | 1.94 | 0.50 | 0.62 | 0.44 |
| C22:5n3 | 0.44 | 1.31 | 0.66 | 0.73 | 0.47 | 0.49 | 0.57 | 0.44 |
| C22:6n3 | 1.24 | 1.65 | 0.99 | 2.26 | 1.67 | 1.70 | 1.69 | 1.24 |
| SUM | 100 | 100 | 100 | 100 | 100 | 100 | 100 | 100 |

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A method for raising a rabbit comprising feeding said rabbit a feed comprising a source of long-chain fatty acid, wherein the mortality rate of said rabbit is reduced compared to a rabbit raised in the absence of said long-chain fatty acid source.

2. The method of claim 1, wherein said mortality rate is decreased by at least about 50%.

3. The method of claim 1, wherein said mortality rate is decreased by at least about 65%.

4. The method of claim 1 wherein said long-chain fatty acid source comprises at least 10% (as % by weight total fatty acids) omega-3 long-chain fatty acid and at least 5% omega-6 long-chain fatty acid.

5. The method of claim 1 wherein said long-chain fatty acid source comprises at least 15% (as % by weight total fatty acids) omega-3 long-chain fatty acid and at least 10% omega-6 long-chain fatty acid.

6. The method of claim 1 wherein the long-chain fatty acid content of a thigh or loin of said rabbit is increased by at least about 50%.

7. The method of claim 1 wherein said long-chain fatty acid source comprises a marine source.

8. The method of claim 1 wherein said long-chain fatty acid source comprises a marine source selected from the group consisting of fish oil, fish meal and microorganisms.

9. The method of claim 1 wherein said long-chain fatty acid source comprises microorganisms.

10. The method of claim 1 wherein said microorganisms are in a dry form.

11. The method of claim 1 wherein said microorganisms are of the order Thraustochytriales.

12. The method of claim 1 wherein said microorganisms are selected from the group consisting of Thraustochytrium, Schizochytrium, and mixtures thereof.

13. The method of claim 1 wherein said long-chain fatty acid source comprises a long-chain fatty acid selected from the group consisting of linolenic acid, gammalinolenic acid, dihomogammalinolenic acid, stearidonic acid, eicosapentaenoic acid, docosapentaenoic acid (both omega-3 and omega-6 forms), docosahexaenoic acid, arachidonic acid, and mixtures thereof.

14. The method of claim 1 wherein said long-chain fatty acid source comprises docosahexaenoic acid.

15. The method of claim 1 wherein said feed comprises at least about 0.1% by weight long-chain fatty acid source.

16. The method of claim 1 wherein said feed comprises at least about 0.01% by weight long-chain omega-3 fatty acid.

17. The method of claim 1 wherein said feed comprises at least about 0.003% by weight long-chain omega-6 fatty acid.

18. The method of claim 1 wherein said feed is fed to said rabbit for at least about 5 days.

19. The method of claim 1 wherein said feed comprises from about 0.02% by weight to about 0.12% by weight long-chain omega-3 fatty acid.

20. The method of claim 1 wherein said feed comprises from about 0.008% by weight to about 0.03% by weight long-chain omega-6 fatty acid.

21. A rabbit meat product produced by the method of claim 1.

22. A method for increasing an average daily weight gain of a rabbit comprising feeding said rabbit a feed comprising a long-chain fatty acid source, wherein the average daily weight gain of said rabbit is higher than a rabbit raised in the absence of said long-chain fatty acid source.

23. The method of claim 22, wherein the average daily weight gain of said rabbit is increased by at least about 2%.

24. A method for reducing a feed conversion rate in a rabbit comprising feeding said rabbit a feed comprising a long-chain fatty acid source, wherein the feed conversion rate of said rabbit is lower than a rabbit raised in the absence of said long-chain fatty acid source.

25. The method of claim 24, wherein the feed conversion rate of said rabbit is decreased by at least about 0.03 g/day.

26. The method of claim 24, wherein the feed conversion rate of said rabbit is decreased by at least about 1%.

27. A method for increasing a docosahexaenoic acid content of a rabbit comprising feeding said rabbit a feed comprising a docosahexaenoic acid source, wherein said docosahexaenoic acid source comprises microorganisms.

28. The method of claim 27, wherein said docosahexaenoic acid source comprises a marine source.

29. The method of claim 27, wherein said docosahexaenoic acid source comprises a precursor to docosahexaenoic acid such as linolenic acid, gammalinolenic acid, dihomogammalinolenic acid, stearidonic acid, eicosapentaenoic acid, docosapentaenoic acid (n-3), or mixtures thereof, wherein said precursors can be elongated to docosahexaenoic acid, and the precursors and the subsequent elongation products accumulate in the rabbit meat.

30. The method of claim 27, wherein said docosahexaenoic acid source comprises at least 10% (as % by weight total fatty acids) DHA.

31. The method of claim 27, wherein said feed comprises at least about 0.1% by weight docosahexaenoic acid source.

32. The method of claim 27, wherein said feed comprises at least about 0.01% by weight docosahexaenoic acid.

33. The method of claim 27, wherein the docosahexaenoic acid content of a thigh or loin of said rabbit is increased by at least about 50%.

34. A method for increasing productivity of a rabbit comprising feeding said rabbit a feed comprising a source of long-chain fatty acid, wherein the productivity of said rabbit is higher compared to a rabbit raised in the absence of said long-chain fatty acid source.

35. The method of claim 34, wherein said productivity is increased by decreasing the mortality rate of said rabbit.

36. The method of claim 34, wherein said mortality rate is decreased by at least about 40%.

37. The method of claim 34, wherein said mortality rate is decreased by at least about 50%.

38. The method of claim 34, wherein said productivity is increased by increasing the average daily weight gain of said rabbit.

39. The method of claim 34, wherein the average daily weight gain of said rabbit is increased by at least about 1%.

40. A method for decreasing the total amount of fat of a rabbit comprising feeding said rabbit a feed comprising a source of long-chain fatty acid, wherein the total amount of fat of said rabbit is lower compared to a rabbit raised in the absence of said long-chain fatty acid source.

41. The method of claim 40, wherein said total amount of fat of said rabbit is decreased by at least about 5%.

42. The method of claim 40, wherein said total amount of fat of said rabbit is decreased by at least about 10%.

43. A method for raising a female rabbit for breeding comprising feeding said female rabbit a feed comprising a source of long-chain fatty acid during one or more time periods selected from the group comprising the time period prior to pregnancy, the time period during pregnancy and the time period during lactation, wherein one or more of the characteristics selected from the group comprising fertility, growth, mortality and immunity of said female rabbit or the offspring of said female rabbit is improved compared to a female rabbit or offspring raised in the absence of said long-chain fatty acid source.

44. A method for increasing a long-chain fatty acid content of a rabbit comprising feeding said rabbit a feed comprising a long-chain fatty acid source, wherein said long-chain fatty acid source comprises microorganisms.

* * * * *